United States Patent [19]

Burks, Jr.

[11] Patent Number: 4,665,243
[45] Date of Patent: May 12, 1987

[54] PROCESS FOR PREPARING VINYL CHLORIDE MONOMER

[75] Inventor: William M. Burks, Jr., Yorktown Heights, N.Y.

[73] Assignee: Stauffer Chemical Company, Westport, Conn.

[21] Appl. No.: 447,869

[22] Filed: Dec. 8, 1982

[51] Int. Cl.$^4$ ............................................. C07C 17/34
[52] U.S. Cl. ................................... 570/226; 570/227
[58] Field of Search .............................. 570/226, 227

[56] References Cited

U.S. PATENT DOCUMENTS

| | | | |
|---|---|---|---|
| 2,569,923 | 10/1951 | Chevey | 570/226 |
| 2,981,764 | 4/1961 | Bihan et al. | 570/227 |
| 3,290,399 | 12/1966 | Braconier et al. | 570/227 |
| 3,843,736 | 10/1974 | Rechmeier et al. | 570/226 |
| 4,347,391 | 8/1982 | Campbell | 570/252 |
| 4,351,819 | 9/1982 | Riegel et al. | 423/488 |

FOREIGN PATENT DOCUMENTS

| | | | |
|---|---|---|---|
| 1186716 | 2/1959 | France . | |
| 42766 | 10/1977 | Japan | 570/227 |

OTHER PUBLICATIONS

J. Barnwell and C. P. Morris, "Heat Pump Cuts Energy Use", Hydrocarbon Processing, Jul., 1982, pp. 117–119.
G. P. Quadri, "Use Heat Pump for P—P Splitter", Hydrocarbon Processing, Feb. 1981.
G. P. Quadri, "Use of Heat Pump for P—P Splitter", Hydrocarbon Processing, Mar. 1981.
Vinyl Chloride–PPG Industries, Inc. Hydrocarbon Processing, Nov. 1981.
Vinyl Chloride–(BFGoodrich Process) The BFGoodrich Co. Hydrocarbon Processing, Nov. 1981.
Vinyl Chloride–Stauffer Chemical Co. Hydrocarbon Processing, Nov. 1981.
Process for the Production of Vinyl Chloride Brochure of Stauffer Chemical Company.
Vinyl Chloride Monomer . . . What You Should Know by McPherson et al., Hydrocarbon Processing, Mar., 1979, pp. 75–88.
Cono–meth and Super–meth, Hydrocarbon Processing Apr., 1982, pp. 152 and 155.
Paper entitled Distillation Column with Vapor Recompression by R. Danziger, Nov. 1978.

Primary Examiner—Natalie Trousof
Assistant Examiner—Joseph A. Boska
Attorney, Agent, or Firm—Paul J. Juettner

[57] ABSTRACT

The energy requirements for preparing vinyl chloride monomer can be reduced by a process which includes the steps of purifying by distillation ethylene dichloride, compressing the ethylene dichloride vapor from the distillation column to a temperature and pressure sufficient for direct feed to a pyrolysis furnace. Up to 80% of the heat presently used after distillation and before pyrolysis can be saved.

4 Claims, 1 Drawing Figure

PROCESS FOR PREPARING VINYL CHLORIDE MONOMER

The present invention relates to a process and apparatus for preparing vinyl chloride monomer and particularly to an energy saving process improvement therefor.

BACKGROUND OF THE INVENTION

Vinyl chloride is prepared by cracking ethylene dichloride vapor at elevated temperature and pressure in a pyrolysis zone. The ethylene dichloride can be prepared by reacting ethylene with chlorine in a low or high temperature reaction such as disclosed in U.S. Pat. No. 4,347,391. The ethylene dichloride can also be prepared by the oxychlorination reaction of ethylene, a source of oxygen and hydrogen chloride. Each reaction does not form pure ethylene dichloride. The reaction products include heavy ends such as 1,1,2-trichloroethane, 1,1,1,2- or 1,1,2,2 tetrachloroethane, pentachloroethane and light ends such as air, hydrogen chloride, hydrogen, chlorine, ethylene, low boiling chlorinated hydrocarbons and the like. The ethylene dichloride is purified to at least about 98% purity by distillation. Various distillation procedures are available and are well known to those skilled in the art.

Two general distillation methods are used. The first uses sequential reflux columns to remove first the light ends and non-condensables (light ends column) and second to separate the ethylene dichloride from the heavy ends principally 1,1,2-trichloroethane (heavy ends column). In an alternative method such as shown in U.S. Pat. No. 4,347,391, controlled steam flow in a single column allows the light ends and non-condensables to be removed out of the top of the column, the ethylene dichloride to be concentrated and can be taken off as a liquid in the center of the column or as a vapor and the heavy ends to be removed from the bottom of the column.

The ethylene dichloride vapor is generally taken from the distillation column at a temperature within the range of about 85° C. to 120° C. at a pressure of atmospheric to about 2.0 kilograms per square centimeter gauge. The vapor is condensed, the product cooled to about 40° C., and pumped into a storage tank. The product is pumped from the storage tank to the pyrolysis furnace. The ethylene dichloride is vaporized by applying heat, usually in the form of steam, in a heat transfer means to elevate the temperature of the vapor to about 185° C. and a pressure of about 10.0 kilograms per square centimeter gauge. An optional preheater system has been employed whereby the ethylene dichloride liquid is passed through a coil heated by the exhaust gases of the pyrolysis furnace or by heat interchange with another process fluid. In each instance, the preheating and vaporization of the ethylene dichloride to the proper temperature and pressure for entrance to the pyrolysis zone requires approximately 340 kilocalories per kilogram of vinyl chloride monomer produced.

BRIEF SUMMARY OF THE INVENTION

In accordance with the invention, the energy necessary to provide ethylene dichloride vapor at the level of temperature and pressure required for entrance into the pyrolysis furnace can be significantly reduced by a process which comprises conducting a substantially saturated vapor of ethylene dichloride to a compressor, compressing the vapor from a pressure ranging from atmospheric to 2 kilograms per square centimeter gauge to a pressure ranging from about 6 to about 14 kilograms per square centimeter gauge and pyrolyzing the compressed vapor. By this process, the energy needed for this portion of the process can be reduced to about 1/6 without any contemplated loss in yield. The amount of energy required was determined mathematically.

DETAILED DESCRIPTION OF THE INVENTION

Figure 1:
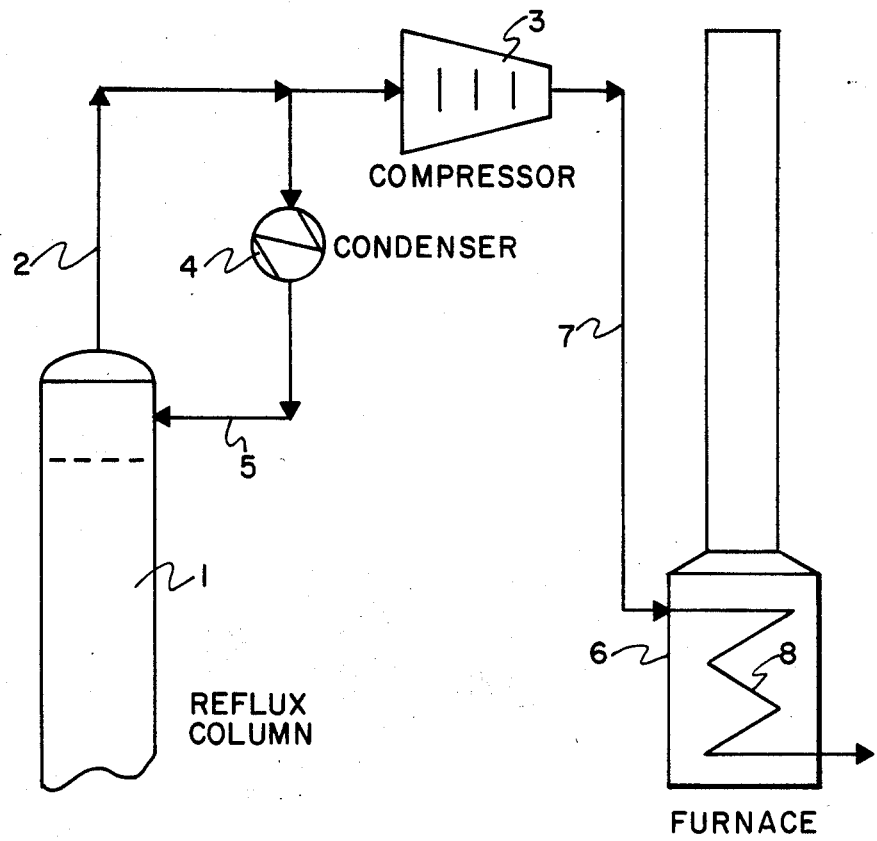
FIG. 1 is a schematic diagram of the process and apparatus of the invention.

Reference is made to FIG. 1 wherein the ethylene dichloride vapor is conducted from reflux column 1 through line 2 to compressor 3. The reflux column is preferably a heavy ends column. The ethylene dichloride vapor is at a temperature of at least 85° C. and preferably at a temperature from about 85° C. to about 120° C. The ethylene dichloride is at the vapor pressure at that temperature. The pressure generally ranges from about atmospheric pressure to about 2 kilograms per square centimeter gauge.

A portion of the vapor is condensed in condenser 4 and returned via line 5 to the reflux column 1 to provide reflux. Reflux can also be provided by the use of an external source of ethylene dichloride. Rates of reflux are well known to those skilled in the art. Reflux ratios for commercial units range from about 0.7 to 1.0 up to about 1.5 to 1.0.

The remaining vapor is compressed in compressor 3 sufficient to provide ethylene dichloride vapor at a pressure and temperature sufficient for feed to the pyrolysis furnace. The compressor can be any mechanical compressor which is adapted for gas compression such as a reciprocating compressor, screw compressor, preferably a centrifugal compressor, and the like. The compressor can be single stage or multiple stage depending upon the design. Since the compressor has to provide a heated vapor at elevated pressure, the compressor should be insulated and provided with proper temperature control means such as heating fluids in a jacket or other equivalent devices to prevent condensation. Further heating can be applied beyond the compressor and before the pyrolysis furnace if necessary.

The compressed ethylene dichloride vapor is conducted to the pyrolysis furnace 6 through line 7 into coil 8 located within the furnace. The ethylene dichloride is thermally cracked in the furnace providing vinyl chloride monomer and hydrogen chloride. Temperatures of pyrolysis or cracking are well known and do not form a part of this invention.

The vinyl chloride, hydrogen chloride and unreacted ethylene dichloride are separated with the hydrogen chloride being recycled to an oxychlorination process (not shown) such as that shown in U.S. Pat. No. 4,347,391 for conversion to further ethylene dichloride. Any unreacted ethylene dichloride after purification is recycled. The vinyl chloride monomer is purified to provide the final product.

Maintenance of proper temperature and pressure in the pyrolysis zone is essential to the purity of the vinyl chloride monomer and other down stream processing. The hydrogen chloride is separated from the vinyl chloride and ethylene dichloride under pressure to allow for the separation without distilling off the vinyl chloride. The hydrogen chloride under pressure can be condensed using commercial refrigeration equipment and a portion recycled for reflux. Maintenance of a pressure at the entrance of the pyrolysis zone within the range of from about 6 to about 14, preferably from about 9 to about 11 kilograms per square centimeter gauge, is desirable for efficient results.

Since energy savings are of prime importance, all lines, vessels and equipment are preferably insulated and if necessary jacketed for proper temperature control. The temperature of the ethylene dichloride vapor from the distillation column to the compressor should not be allowed to decrease as this requires an input of heat to maintain proper temperature and to avoid condensation.

The present invention is not intended to be limited to the manner of obtaining the ethylene dichloride vapor as long as a relatively pure vapor (at least 96% and preferably at least 98% ethylene dichloride) is used.

The present invention can not only be utilized as part of a new process but can also be advantageously used as part of an existing process.

Existing apparatus can be modified to by-pass the present system which includes a condensation means, storage tank, optional preheater and vaporizer by taking the feed from the top of the reflux condenser and conducting the major portion of that feed through the compressor using the existing condenser to partially condense a small portion of the feed for recycle for reflux. In case of an emergency or overcapacity in the main system, the secondary system can be used to condense the ethylene dichloride and store the same. A similar storage system could be added to new construction but this is not essential.

The present invention will be further illustrated in the following proposed example:

EXAMPLE

Ethylene dichloride at approximately 98% purity and at a vapor pressure of about 1.0 kilograms per square centimeter gauge is compressed using a multi-stage centrifugal compressor with insulation. The energy required to provide the ethylene dichloride to the pyrolysis furnace at a pressure of about 10.0 kilograms per square centimeter gauge and a temperature of about 185° C. is about 720,000 kilocalories per hour based on a feed rate to the pyrolysis furnace of 40,000 kilograms of purified ethylene dichloride per hour.

In a conventional system, purified liquid ethylene dichloride at about 40° C. is taken from a storage tank and preheated and vaporized to a temperature of about 185° C. and a pressure of about 10.0 kilograms per square centimeter gauge. Based on a feed rate of 40,000 kilograms per hour, about 4,250,000 kilocalories per hour is required to provide the ethylene dichloride to the pyrolysis furnace using the conventional process.

The process of the present invention requires only 1/6 of the energy required in providing the feed to the pyrolysis furnace vis-a-vis the energy required in the conventional process.

What is claimed is:

1. A process for preparing vinyl chloride monomer from ethylene dichloride which comprises:
    (a) mechanically compressing an ethylene dichloride vapor to a pressure within the range of from about 6 to about 14 kilograms per square centimeter gauge to provide a vapor of sufficient temperature and pressure for use as a feed for pyrolysis to a vinyl chloride monomer; and
    (b) pyrolyzing the vapor to form vinyl chloride monomer and hydrogen chloride.

2. A process for conserving energy during the manufacture of vinyl chloride monomer from ethylene dichloride comprising:
    (a) forming a purified vapor of ethylene dichloride by distillation at a pressure from about atmospheric pressure up to about 2.0 kilograms per square centimeter gauge;
    (b) mechanically compressing the ethylene dichloride vapor to a pressure within the range of from about 6 to about 14 kilograms per square centimeter gauge; and
    (c) pyrolyzing the compressed vapor to form vinyl chloride monomer and hydrogen chloride said ethylene dichloride vapor being fed to the compression step (b) and the pyrolysis step (c) is maintained at a temperature above its condensation point.

3. The process according to claim 2 wherein the ethylene dichloride vapor is compressed to a pressure within the range of from about 9 to about 11 kilograms per square centimeter gauge.

4. The process according to claim 2 wherein a portion of the ethylene dichloride vapor prior to compression is condensed and returned as reflux in the distillation.

* * * * *